(12) United States Patent
Subramony et al.

(10) Patent No.: US 11,077,254 B2
(45) Date of Patent: Aug. 3, 2021

(54) EMBEDDED MULTIPLE-PART SENSOR WITHIN A PLUNGER ROD TO CAPTURE AND TRANSIT INJECTION INFORMATION

(71) Applicant: MEDIMMUNE, LLC, Gaithersburg, MD (US)

(72) Inventors: Janardhanan Anand Subramony, Gaithersburg, MD (US); Michael C. Song, Gaithersburg, MD (US)

(73) Assignee: MEDIMMUNE, LLC, Gaithersburg, MD (US)

( * ) Notice: Subject to any disclaimer, the term of this patent is extended or adjusted under 35 U.S.C. 154(b) by 229 days.

(21) Appl. No.: 16/469,211

(22) PCT Filed: Dec. 13, 2017

(86) PCT No.: PCT/US2017/065965
§ 371 (c)(1),
(2) Date: Jun. 13, 2019

(87) PCT Pub. No.: WO2018/111969
PCT Pub. Date: Jun. 21, 2018

(65) Prior Publication Data
US 2019/0344019 A1 Nov. 14, 2019

Related U.S. Application Data

(60) Provisional application No. 62/434,131, filed on Dec. 14, 2016.

(51) Int. Cl.
*A61M 5/31* (2006.01)
*A61M 5/315* (2006.01)

(52) U.S. Cl.
CPC . *A61M 5/31568* (2013.01); *A61M 2205/0216* (2013.01); *A61M 2205/3317* (2013.01); *A61M 2205/3584* (2013.01)

(58) Field of Classification Search
CPC ............ A61M 5/3135; A61M 5/31511; A61M 5/31525; A61M 5/31565; G16H 10/20;
(Continued)

(56) References Cited

U.S. PATENT DOCUMENTS 4,713,060 A 12/1987 Riuli
5,704,922 A 6/1998 Brown
(Continued)

FOREIGN PATENT DOCUMENTS

EP 3439191 A1 2/2019

*Primary Examiner* — Nathan R Price
*Assistant Examiner* — Courtney B Fredrickson

(57) ABSTRACT

A smart plunger rod adapted to push a medication out of a syringe is disclosed. The plunger rod comprises a shaft sized and dimensioned to act on a piston on the syringe and a finger actuated head portion containing at least two subunits of a wireless sensor. In a pre-activation configuration, the subunits are spaced apart from each other by a physical barrier and the wireless sensor is non-operational. In a post-activation configuration, the subunits are connected to each other and the sensor is operational to send a signal. A user activates the finger actuated head portion to reversibly move the physical barrier and moves the plunger rod from the pre-activation configuration to the post-activation configuration. The signal sent by the sensor comprises information relating to ejecting the medication out of the syringe, and is received by a remote receiver.

13 Claims, 11 Drawing Sheets

(58) Field of Classification Search
CPC ........ G16H 10/60; G16H 20/10; G16H 20/17; G16H 50/30
See application file for complete search history.

(56) References Cited

U.S. PATENT DOCUMENTS

| | | | |
|---|---|---|---|
| 9,186,465 B2* | 11/2015 | Jorgensen | A61M 5/31551 |
| 2002/0143288 A1* | 10/2002 | Larsen | A61M 5/31551 |
| | | | 604/19 |
| 2006/0036209 A1 | 2/2006 | Subramony et al. | |
| 2007/0025890 A1* | 2/2007 | Joshi | C25B 1/13 |
| | | | 422/186.07 |
| 2011/0313395 A1* | 12/2011 | Krulevitch | A61M 5/3129 |
| | | | 604/504 |
| 2014/0005950 A1 | 2/2014 | Groeschke et al. | |
| 2015/0005703 A1 | 1/2015 | Hutchinson et al. | |
| 2015/0246179 A1 | 3/2015 | Zur et al. | |
| 2016/0015903 A1* | 1/2016 | Madsen | A61M 5/31553 |
| | | | 604/211 |
| 2016/0074587 A1 | 3/2016 | Searle et al. | |
| 2016/0151558 A1* | 6/2016 | Tobescu | G06K 19/07705 |
| | | | 604/111 |
| 2016/0287788 A1 | 10/2016 | Tremblay et al. | |
| 2018/0333543 A1* | 11/2018 | Diaz | A61M 5/3232 |
| 2019/0321555 A1* | 10/2019 | Biondi | A61M 5/3157 |

* cited by examiner

FIGURE 1
FIGURE 2
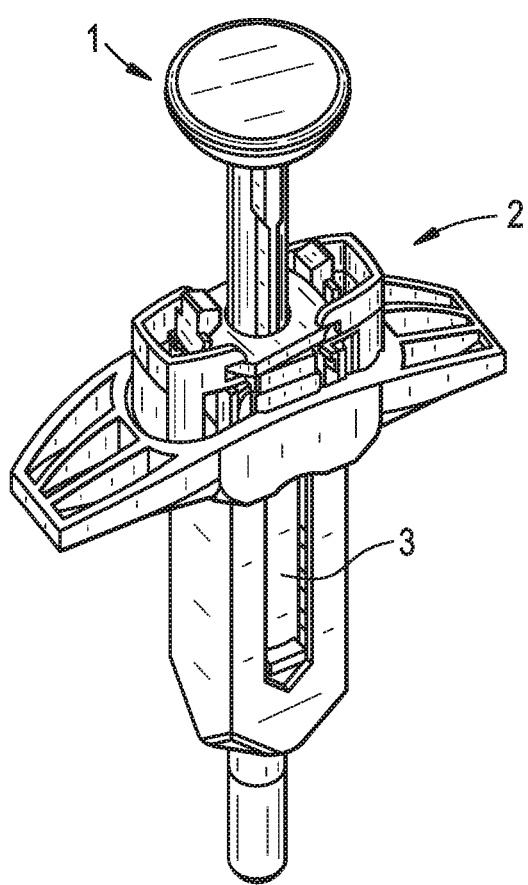
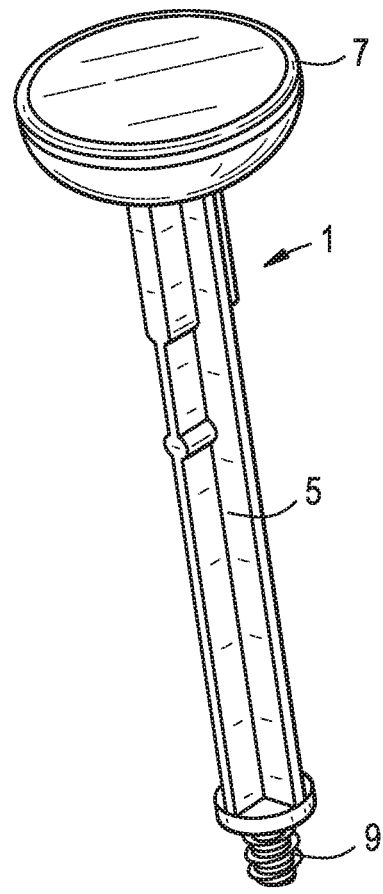

EMBEDDED MULTIPLE-PART SENSOR WITHIN A PLUNGER ROD TO CAPTURE AND TRANSIT INJECTION INFORMATION

CROSS-REFERENCE TO RELATED APPLICATIONS

This application is a U.S. National Stage application of International Application No. PCT/US2017/065965, filed on Dec. 13, 2017, said International Application No. PCT/US2017/065965 claims benefit under 35 U.S.C. § 119(e) of the U.S. Provisional Application No. 62/434,131, filed Dec. 14, 2016. Each of the above listed applications is incorporated by reference herein in its entirety for all purposes.

FIELD OF THE INVENTION

The present invention relates generally to a sensor and communication system that can be integrated within a syringe plunger rod to confirm syringe injection and to transmit such information wirelessly.

BACKGROUND OF THE INVENTION

In ensuring optimal patient treatment, it is essential for patients to comply with the medication regiments prescribed by their health care provider (HCP). Similarly, because no two patients are identical, to ensure the best care and medication prescribed for the patient, the HCPs need to know that the patient is in compliance with taking his/her prescribed medication. This information will help HCPs to determine if the medication is working for the patient or a better alternative medication regiment may be benefit the patient more.

Similarly, knowing that patients complied with prescriptions is necessary to determine the efficacy of new medications in clinical trials. In clinical trials, prefilled syringes are commonly used, and often a new drug will be introduced into the market in prefilled syringes first to be followed by more complex delivery devices such as autoinjectors, etc.

Currently, there are no sensor or electronic system embedded with prefilled syringes or accessorized prefilled syringes that can provide the HCPs with confirmation of syringe injection usage, which can then be used to correlate medication compliance with treatment efficacy. Today, the HCPs rely on the patients to report medication compliance and on their truthfulness outside of the clinical setting. This reliance on patient truthfulness in taking the prescribed medication regiment can be a significant risk in clinical trials, where the investigative new drug's efficacy, benefits and other results depend heavily on the patients' compliance with the prescribed medication regiment.

Prior art utilizes physical and electronics journals to keep track of patient medication regiment. In addition, other prior art consist of electronic reminders to remind patients to take their medication. Both of these systems are passive and depended on patient truthfulness and compliance, and are only marginally effective. A HCP will not be able to tell if, for example, a patient simply fill in their journals right before going in to see their HCP to show compliance, when the patient had not been compliant. Similarly, with the electronic reminders the patient may simply indicate injection to silence the alarms without actually injecting the medication.

As such, there exists a need for a means and apparatus to capture actual syringe usage and other confirmation information and to transmit such information for example wirelessly to ensure patient compliance and allow the HCPs to determine the efficacy of the medication.

SUMMARY OF THE INVENTION

Hence, the present invention is directed to methods, designs, and apparatuses for detecting syringe injection and transmitting the injection confirmation information wirelessly to an external receiver. The invention employs the separation of the one or more subunits or subsystems within a wireless transmission system, whereby the subunits are embedded within the syringe plunger rod and kept separate prior to use. When the syringe is injected/used by the user depressing the plunger rod, the separated wireless transmission subunits are brought together and electrically reconnected establishing an operating wireless transmission system.

The separation of the wireless transmission subsystems, such as the antenna and the wireless transmission chip subsystems, also creates a sensor that detects whether the syringe was injected into the patient. For example, when the antenna and transmission chip subsystems are connected, the sensor is operable after plunger rod has been depressed to confirm syringe injection. At the same time, the sensor transmits the injection confirmation signal to a receiver.

Thus, the wireless transmission system can be that of a Bluetooth chip and Bluetooth antenna or any other wireless transmission system, whereby the antenna and the integrated and/or transmission chip(s) can be separated to create a confirmation sensor setup.

To ensure that the antenna and the transmission chip are kept separated and would not unintentionally come together prior to a successful injection, the transmission chip and antenna subsystems are kept separated by a physical barrier that is overcome during injection. During injection, when the plunger rod is depressed by the user, the antenna for example overcomes the physical barrier and comes into contact with the transmission chip to form a complete and operable wireless transmission system which captures and/or transmits the injection confirmation data.

This subject invention can be integrated within any plunger and utilized for all syringes including but not limited to prefilled syringes intended to be injected using a plunger rod, including but not limited to autoinjectors. The subject invention creates a digital connectivity plunger rod for injection syringes.

BRIEF DESCRIPTION OF THE DRAWINGS

In the accompanying drawings, which form a part of the specification and are to be read in conjunction therewith and in which like reference numerals are used to indicate like parts in the various views:

FIG. 1 is a perspective view of a prefilled syringe comprising of a passive safety device, a syringe, and an inventive digitally connected plunger rod;

FIG. 2 is a perspective view of an assembled digital connectivity plunge rod from FIG. 1;

DETAILED DESCRIPTION OF THE PREFERRED EMBODIMENTS

As discussed above, the present invention includes separating a wireless sensor into two or more subunits or parts and keeping the subunits separated within an inventive digitally connected plunger rod in the pre-activation configuration. When its subunits are separated the wireless sensor is preferably non-operational and cannot transmit signals. More preferably, the sensor's subunits are physically separated by a physical barrier that can be overcome with a sufficient force, preferably substantially similar to a force necessary to depress the plunger rod to expel all the medication from the syringe.

During activation, a user presses the plunger rod thereby applying this force on a top of the plunger rod. This force overcomes the physical barrier separating the subunits and assembles or connects the subunits to complete the sensor, allowing the sensor to be operational and sending a signal to a receiver that the injection is completed. In the post-activation configuration, i.e., when all the medication is expelled from the syringe, preferably the physical barrier can resume its original configuration and applies a pressing force keeping the subunits in contact with each other.

In one embodiment, the subunits of the sensor may comprise an antenna/antenna holder and a transmission chip and contact switch assembly. In another embodiment, the contact switches can be grouped with the antenna/antenna holder with the power source separated as in the case of Bluetooth Systems Other embodiment may include isolated or separating out any component or subsystem that comprise the communication system.

Figure 14:
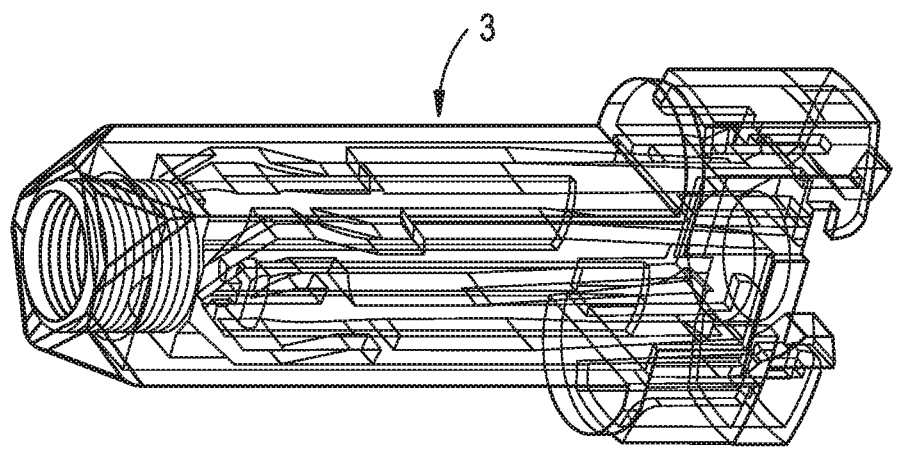
FIG. 14 is a 3D CAD example of a passive syringe component/device.
Figure 15:
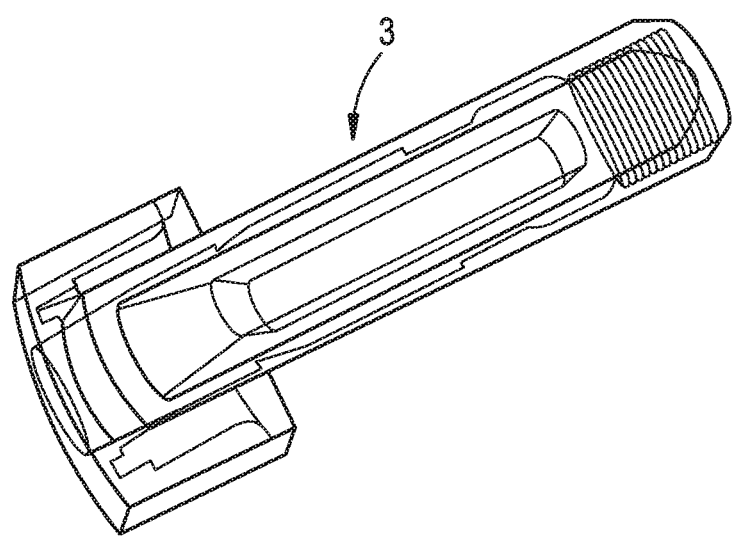
FIG. 15 is a picture of a physical passive syringe safety component/device.

Referring to FIG. 1, an exemplary, inventive digitally connected plunger rod 1 is shown as a part of a syringe unit with a passive syringe safety component 2, and a syringe 3, preferably a pre-filled syringe, with a sheath on its distal end covering a needle. A 3D CAD example of a passive syringe component/device is shown in FIG. 14. A physical picture of the passive syringe safety component/device is shown in FIG. 15. Inventive plunger rod 1 may have shaft 5 and finger actuated head portion 7, as shown FIG. 2. The distal end 9 of shaft 5 is sized and dimensioned to engage a rubber piston within the syringe to push the piston in the distal direction to expel the medication out of the syringe.

Figure 3A:
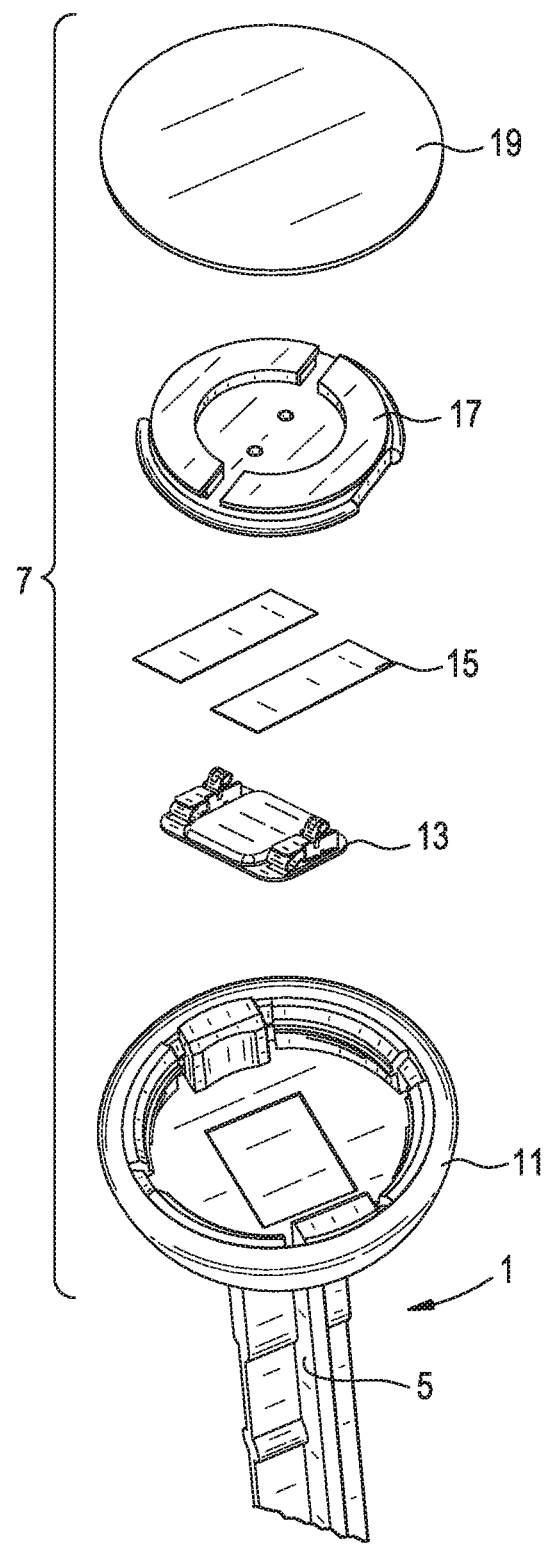
FIG. 3A is an exploded view of the digital connectivity plunger rod from FIG. 2 with the antenna wire omitted for clarity.
Figure 3B:
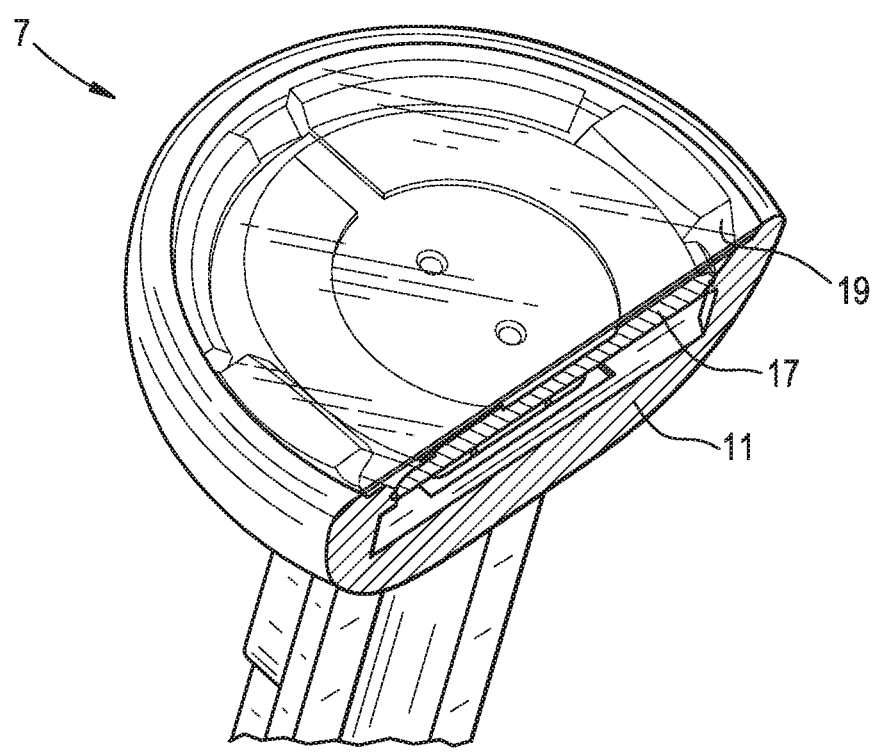
FIG. 3B is a top, cross-sectional perspective view of the top of the plunger rod from FIG. 3A showing the antenna holder being retained within the plunger rod by the elastomeric cover.

As shown in FIG. 3A, user actuatable portion 7 of inventive plunger rod 1 has a sensor holder 11, described in detail below, positioned on top of shaft 5 and the wireless sensor generally comprises a wireless transmission chip and contact switch assembly 13, one or more electrically conductive strip(s) 15 and an antenna holder 17 with an antenna, described below. Conductive strip 15 has a conductive metallic foil with an electrically conductive adhesive coated on one side of the foil. Assembly 13, conductive strip(s) 15 and antenna holder 17 with antenna wire make up the sensor, and a cover 19, which is preferably flexible and more preferably elastomeric, encloses the sensor within sensor holder 11. An assembled user actuatable portion 7 is shown in FIG. 3B.

Figure 4:
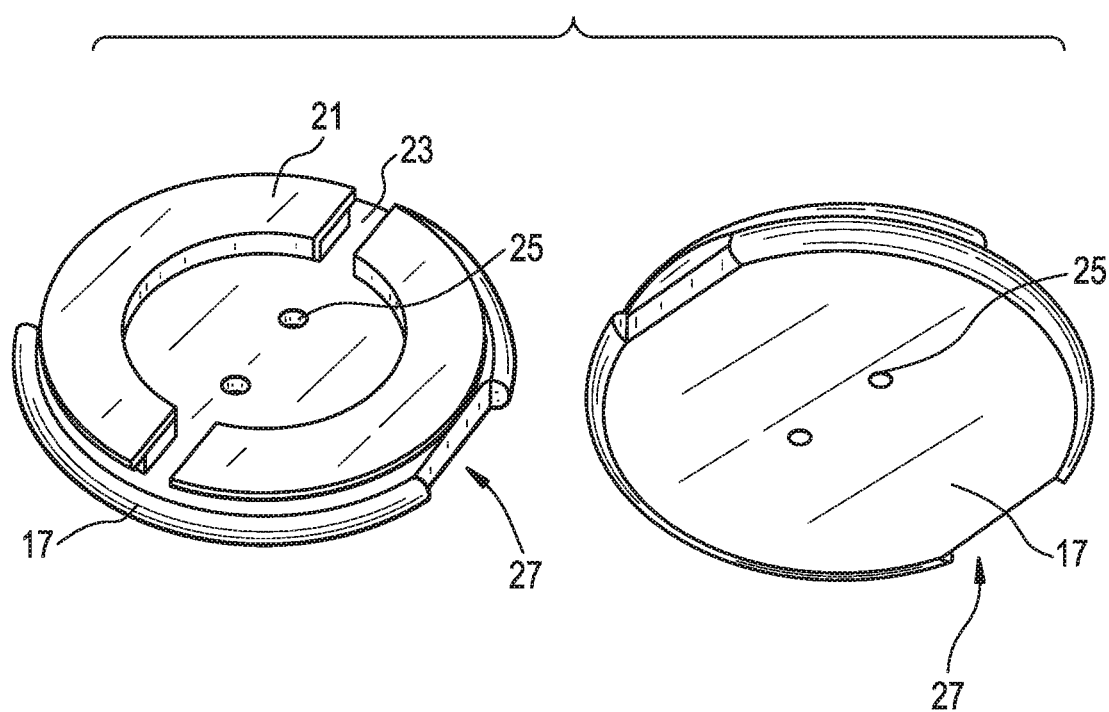
FIG. 4 includes a top and a bottom perspective views of an antenna holder and its components with the antenna wire omitted for clarity.

Antenna holder 17, illustrated with both top and bottom perspective views in FIG. 4, has antenna wire loop holders 21, which comprise two semi-circular shapes defining a wiring channel 23 therebetween. Antenna holder 17 also has two wiring through holes 25 for the antenna wires to pass through holder 17. Antenna holder 17 further comprises at least one orientation guide or notch 27 to guide the orientation of antenna holder 17 within sensor holder 11.

Figure 5:
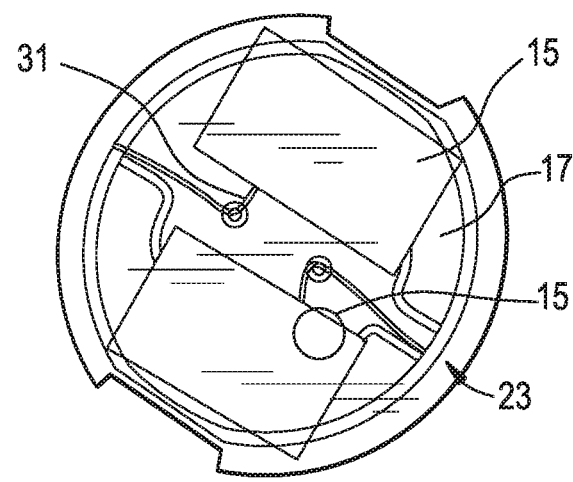
FIG. 5 is an image of the bottom side of the antenna holder showing the ends of the antenna wire being attached to the conductive strips.
Figure 6:
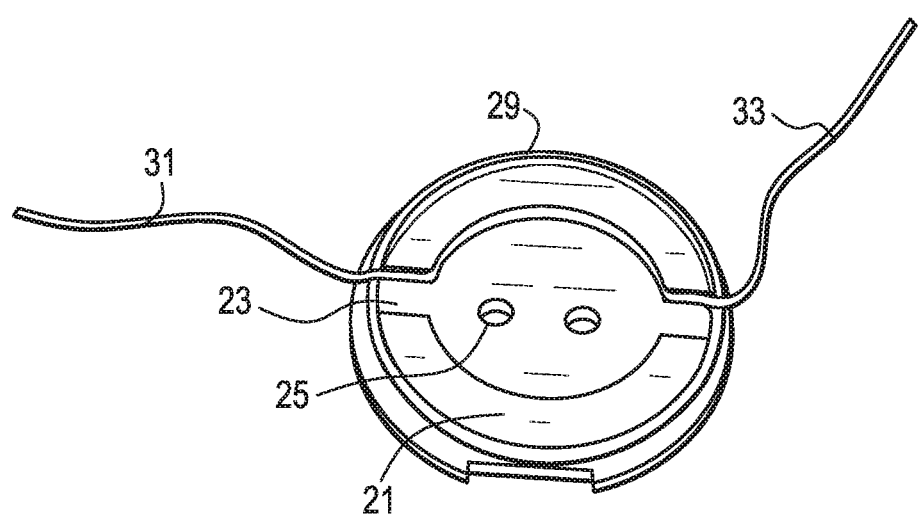
FIG. 6 is an image of the top side the antenna holder showing the antenna wire being wrapped around the antenna holder with the free ends of the antenna wire being unattached.

As best shown in FIGS. 5 and 6, a coil of antenna wire 29 is wrapped around wire loop holders 21. The two ends 31 and 33 of the antenna wire are positioned within wiring channels 23 and threaded through holes 25, and are taped to the bottom surface of antenna holder 17 by the electrically conductive adhesive side of strips 15. Hence, strips 15 on the bottom of antenna holder 17 are electrically connected to the antenna wires wounded on top of antenna holder 17.

Figure 7:
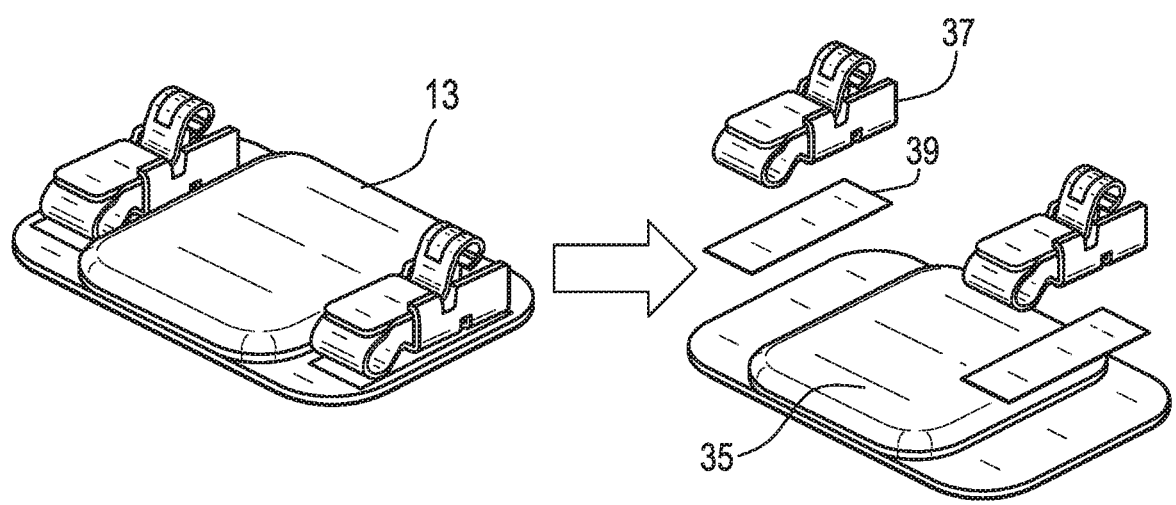
FIG. 7 includes an assembled and an exploded view of the transmission chip system.

Wireless transmission chip and contact switch assembly 13 is best shown in FIG. 7. This assembly comprises a wireless transmission chip 35 and one or more contact switches 37 being attached to chip 35 by conductive, double-sided adhesive strips 39.

Figure 8:
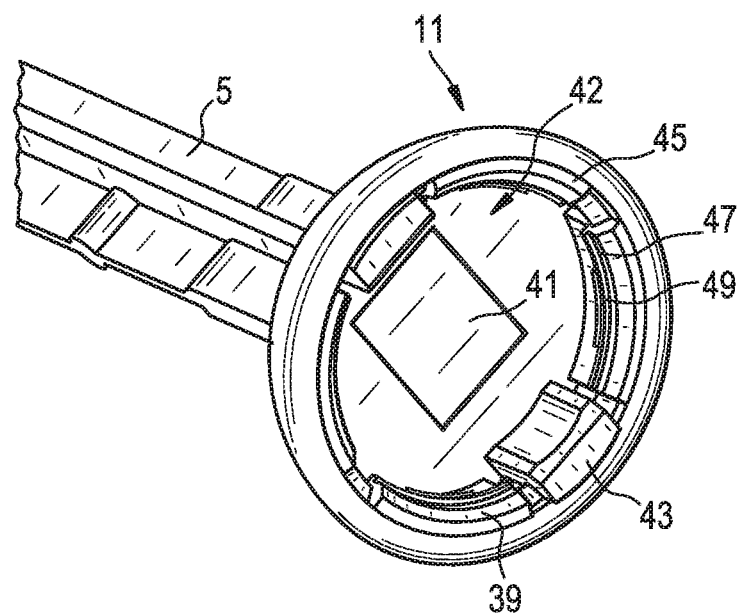
FIG. 8 is a partial top perspective view of the plunger rod without the sensor components and cover for clarity.
Figure 9:
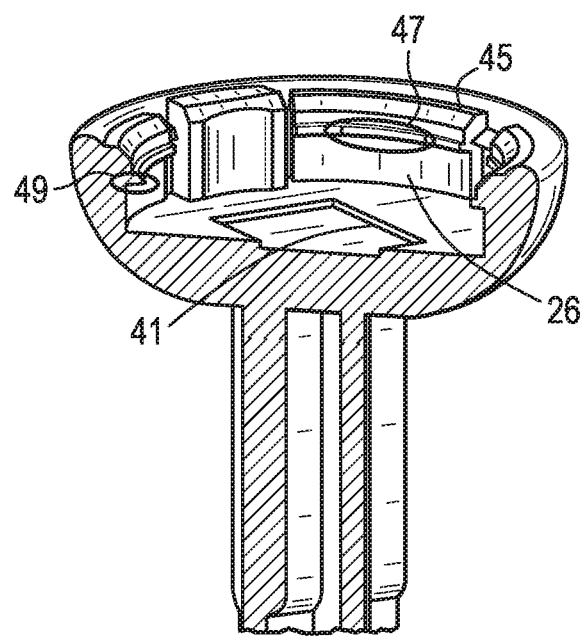
FIG. 9 is a cross-sectional view of the plunger rod from FIG. 7.

Sensor housing 11, as best shown in FIGS. 8 and 9, contains a number of features or physical features to hold the subunits of the sensor, so that these subunits are separated in the pre-activation configuration. Sensor housing 11 has slot or holder 41 sized and dimensioned to receive and hold wireless transmission chip and contact switch assembly 13 on its bottom surface 42, and at least one orientation guide 43 that corresponds to orientation lock or notch 27 on the antenna holder 17. Orientation guide 43 fits into orientation notch 27 to ensure that conductive strips 15 located on the bottom surface of antenna guide 17 are positioned directly above contact switches 37.

Sensor housing 11 also has two supporting surfaces 45 and 47. As best shown in FIG. 9, these two surfaces are formed on an upstanding vertical member; however, this upstanding vertical member may also be formed integrally with the body of sensor housing 11. Supporting surface 45 is located near the top of sensor housing 11, and is adapted to support the outer edge of cover 19. As supported, cover 19 may preferably flex inward when a user pushes plunger rod 1 downward to expel the medication from syringe 3. Cover 19 may be attached to supporting surface 45 by adhesives, spot bonding, ultrasonic welding or other known attachment methods.

Supporting surface 47 is designed to support antenna holder 17 in the pre-activation configuration. Supporting surface 47 is preferably formed by a ledge 49, which is supported in a cantilever fashion from a side of sensor housing 11, as best shown in FIG. 9. Ledge 49 supports antenna holder 17 and is designed to flex downward as plunger rod 1 is pushed by the user. Ledge 49 separates antenna holder 17 away from wireless transmission chip and contact switch assembly 13, so that the sensor is not assembled and not operational in the pre-activation configuration. Ledge 49 provides the physical barrier keeping the subunits of the sensor separated in the pre-activation configuration, as discussed above.

Figure 10:
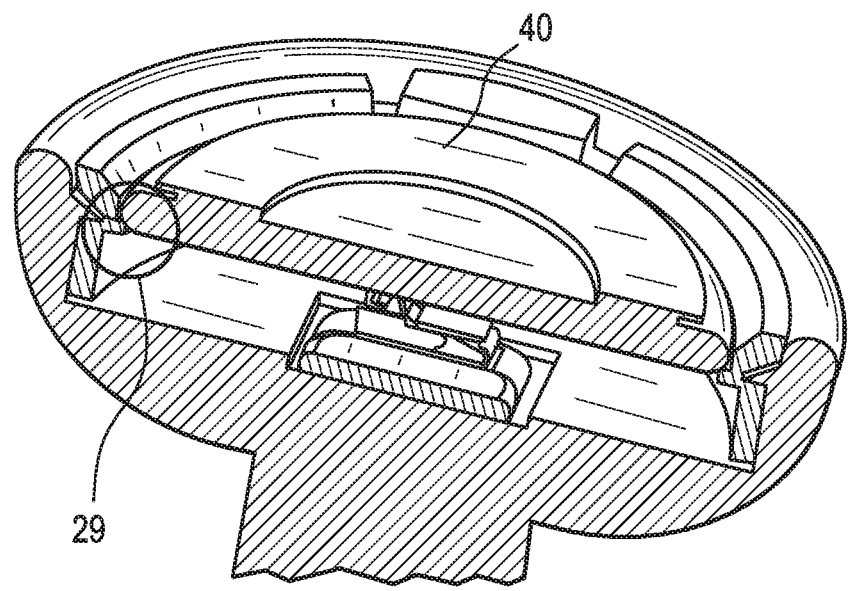
FIG. 10 is a partial, cross-sectional view of the top of the plunger rod showing the antenna holder being placed on top of a barrier in the pre-activation configuration.
Figure 11:
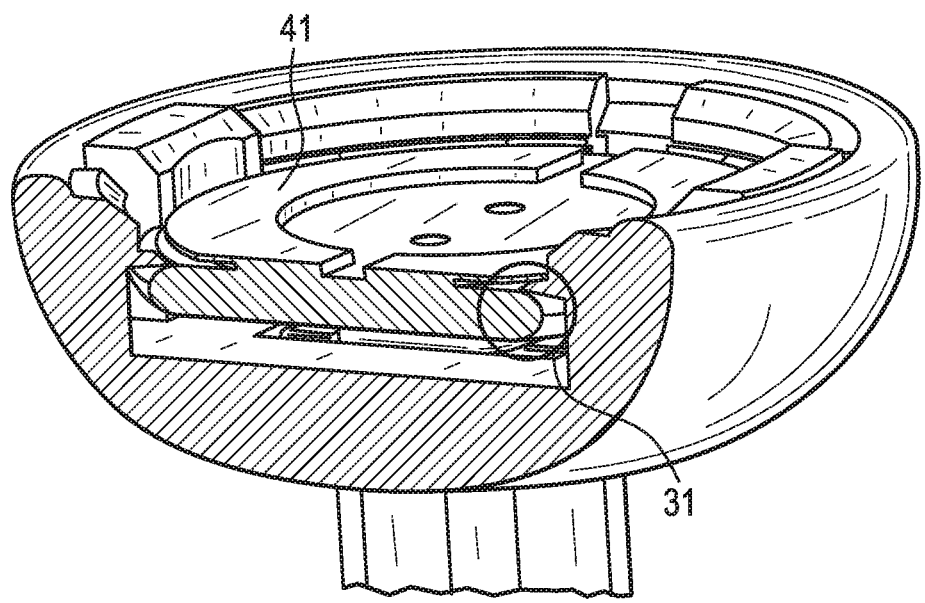
FIG. 11 is a partial, cross-sectional view of the top of the plunger rod similar to that in FIG. 1 in a post-activation configuration.
Figure 12:
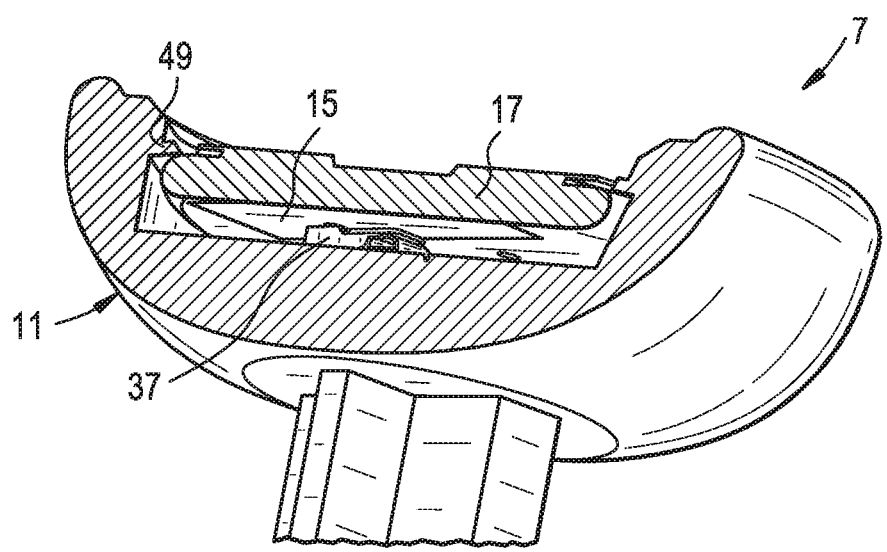
FIG. 12 is a bottom, cross-sectional perspective view of the plunger rod from FIG. 12.

When the user applies a force on the top of plunger rod 1 to eject medication from syringe 3, the same force is applied on head portion 7. This force pushes antenna holder 17 via cover 17, and overcomes ledge 49 and pushes ledge 49 downward allowing antenna holder 17 with antenna wiring to pass therethrough to come into contact with wireless transmission chip and contact switch assembly 13. Contact switches 37 would make electrical contact with conductive strips 15 and the antenna wires. The sequence from pre-activation configuration to post-activation configuration is shown in FIGS. 10-11. In this post-activation configuration, the sensor is assembled and the transmission chip is programmed to send a wireless signal through the antenna in antenna holder 17 to a receiver that the injection of the medication is completed. Preferably, ledge 49 flexes back to return to its original position. In its original position in the post-activation configuration, ledge 49 retains antenna holder 17 in contact with wireless transmission chip and contact switch assembly 13, and preferably ledge 49 due to its flexibility and cantilever connection applies a force keeping antenna holder 17 in contact with wireless transmission chip and contact switch assembly 13. FIG. 12 shows plunger rod 1 in the post-activation configuration with the contact switch 37 in assembly 13 being in contact with conductive strip 15 on the bottom of antenna holder 17. As discussed above, conductive strips 15 are electrically connected to the antenna wire 29 wounded on top of antenna holder 17.

Preferably, the force necessary to overcome the physical barrier or ledge 49 can be designed to be any force level depending on the geometry and how far physical barrier 49 protrudes from the side of sensor housing 11. In other words physical barrier 49 can be a relatively short and thin physical barrier that will require relatively little force to overcome. Conversely, one may add triangular geometry (in the drawings it is sticking out straight), thickness, and length to the physical barrier 49 which will require significantly more force to overcome.

Depending on the force to overcome physical barrier 49, antenna holder 17 can pass the physical barrier toward the beginning, somewhere in the middle, or toward the end of the movement of the plunger. Typically, a low barrier force will mean antenna holder 17 will overcome barrier 49 at the beginning of the movement of plunger 5 during the injection, and a higher barrier force will result in antenna holder 17 to overcome barrier 49 toward the end of the injection. Barrier force somewhere in the middle will result in antenna holder 17 overcoming barrier 49 somewhere during the middle of the injection. The amount of barrier force depends on several factors including material of construct, geometry, thickness, and length/depth that the harder extends out from the side wall. One of ordinary skill in the art may select a proper level of force to overcome the physical barrier from the disclosure of the present invention.

Figure 13:
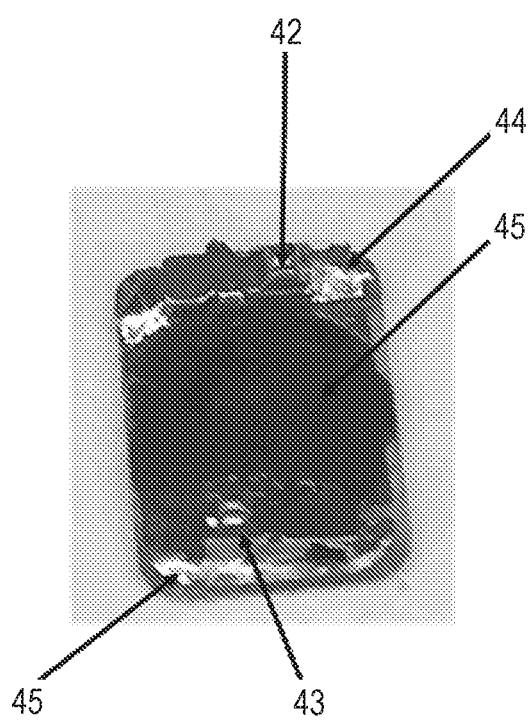
FIG. 13 is an image of an alternative embodiment of the present invention where the contact switches are soldered instead of attachment with conductive adhesive onto the wireless transmission chip.

While it is apparent that the illustrative embodiments of the invention disclosed herein fulfill the objectives stated above, it is appreciated that numerous modifications and other embodiments may be devised by those skilled in the art. One such modification is that the contact switch 37 in assembly 13 is soldered to wireless transmission chip 35, instead of using adhesive strips 39, as shown in FIG. 13. Therefore, it will be understood that the appended claims are intended to cover all such modifications and embodiments, which would come within the spirit and scope of the present invention.

We claim:

1. A plunger rod adapted to push a medication out of a syringe comprising a shaft sized and dimensioned to act on a piston on the syringe and a finger actuated head portion comprising at least two subunits of a wireless sensor,
   wherein in a pre-activation configuration the at least two subunits are spaced apart from each other by a physical barrier and the wireless sensor is non-operational,
   wherein in a post-activation configuration the at least two subunits are connected to each other and the sensor is operational to send a signal,
   wherein a user activates the finger actuated head portion to move the physical barrier and moves the plunger rod from the pre-activation configuration to the post-activation configuration;
   wherein the at least two subunits of the sensors comprises an antenna subunit and a wireless transmission subunit.

2. The plunger rod of claim 1, wherein the physical barrier is flexible and reverts back to an original configuration after being moved.

3. The plunger rod of claim 2, wherein the physical barrier comprises a cantilevered ledge.

4. The plunger rod of claim 1, wherein the antenna subunit comprises an antenna wire wrapped around an antenna holder with at least one electrical lead positioned at the bottom of the antenna holder.

5. The plunger rod of claim 4, wherein the wireless transmission subunit comprises a wireless transmission chip and at least one contact switch.

6. The plunger rod of claim 5, wherein the at least one contact switch contacts the at least one electrical lead in the post-activation configuration.

7. The plunger rod of claim 1, wherein the finger actuated head portion comprises a sensor housing.

8. The plunger rod of claim 7, wherein the sensor housing defines a slot sized and dimensioned to receive the wireless transmission subunit.

9. The plunger rod of claim 8, wherein the sensor housing further comprises an orientation lock sized and dimensioned to match with an orientation notch on the antenna subunit.

10. The plunger rod of claim 1 further comprising a flexible cover located on top of the finger actuated head portion.

11. The plunger rod of claim 10, wherein the flexible cover is elastomeric.

12. The plunger rod of claim 1, wherein the signal comprises information relating to pushing the medication out of the syringe.

13. The plunger rod of claim 1, wherein the signal is received by a remote receiver.

* * * * *